(12) United States Patent
Qian et al.

(10) Patent No.: US 9,194,824 B1
(45) Date of Patent: Nov. 24, 2015

(54) ANVILS AND ULTRA-HIGH PRESSURE APPARATUSES USING THE SAME

(75) Inventors: Jiang Qian, Cedar Hills, UT (US); Kenneth E. Bertagnolli, Riverton, UT (US)

(73) Assignee: US SYNTHETIC CORPORATION, Orem, UT (US)

( * ) Notice: Subject to any disclaimer, the term of this patent is extended or adjusted under 35 U.S.C. 154(b) by 501 days.

(21) Appl. No.: 13/425,647

(22) Filed: Mar. 21, 2012

Related U.S. Application Data

(60) Provisional application No. 61/468,476, filed on Mar. 28, 2011.

(51) Int. Cl.
*G01N 23/20* (2006.01)
*G01N 21/03* (2006.01)

(52) U.S. Cl.
CPC ...... *G01N 23/20041* (2013.01); *G01N 21/0317* (2013.01)

(58) Field of Classification Search
CPC ............ C22C 26/00; B01J 3/00; B01J 3/002; B01J 3/065; B01J 3/06; B01J 3/067; G01N 23/20041; G01N 21/01; G01N 21/0317; G01N 3/04; B30B 11/004; B30B 11/007
USPC ........... 425/77; 356/244; 73/856, 760, 864.91
See application file for complete search history.

(56) References Cited

U.S. PATENT DOCUMENTS

| | | | |
|---|---|---|---|
| 4,081,505 A * | 3/1978 | Kawai | 425/406 |
| 4,636,253 A * | 1/1987 | Nakai et al. | 75/239 |
| 5,011,514 A * | 4/1991 | Cho et al. | 51/295 |
| 6,338,754 B1 | 1/2002 | Cannon et al. | |
| 7,866,418 B2 | 1/2011 | Bertagnolli et al. | |
| 7,998,573 B2 | 8/2011 | Qian et al. | |

OTHER PUBLICATIONS

Kono et al, Elastic properties of sintered diamonds with and without Co binder, Journal of Physics, Conf Series 215, 2010.*
Utsumi et al, High Pressure and High Temperature Generation Using Sintered Diamond Anvils, Geophysical Mongraph Series, High-Pressure Research: Application to Earth and Planetray Sciences, pp. 37-42, vol. 67, 1992.*
U.S. Appl. No. 61/468,476, filed Mar. 28, 2011, Qian et al.
U.S. Appl. No. 11/545,929, filed Oct. 10, 2006, Bertagnolli et al.
Ruoff,et al.; "Yield stress of cemented tungsten carbide"; J. Appl. Phys. 46, No. 11, 4647-4648 (1975); doi:10.1063/1.321542 (2 pages).
Utsumi, et al.; "High-pressure science with a multi-anvil apparatus at SPring-8"; J. Phys.: Condens. Matter 14 (2002) 10497-10504.

(Continued)

*Primary Examiner* — Timothy Kennedy
(74) *Attorney, Agent, or Firm* — Dorsey & Whitney LLP

(57) ABSTRACT

Polycrystalline diamond ("PCD") anvils and associated ultra-high pressure apparatuses employing such anvils. The PCD anvils include an anvil body defining an anvil face. The anvil body comprises a plurality of diamond grains defining a plurality of interstitial regions, with a metal-solvent catalyst occupying at least a portion of the plurality of interstitial regions. The plurality and diamond grains and the metal-solvent catalyst of the PCD collectively exhibit a coercivity of about 115 Oe or more and a specific magnetic saturation of about 15 G·cm³/g or less.

19 Claims, 14 Drawing Sheets

(56) References Cited

OTHER PUBLICATIONS

Tange, et al.; "Pressure generation to 80GPa using multianvil apparatus with sintered diamond anvils"; *High Pressure Research*, vol. 28, No. 3, Sep. 2008, 245-254.

Hemley, et al.; "X-ray imaging of stress and strain of diamond, iron, and tungsten at megabar pressures"; Science 276 (5316): 1242-1245 (1997).

Utsumi, et al.; "X-ray Diffraction under Ultrahigh Pressure Generated with Sintered Diamond Anvils"; Journal of Applied Physics 60 (7) 2201-2204 (1986).

Bundy; "Design Tapered Anvil Apparatus for Achieving Higher Pressures"; Rev. Sci. Instrum., vol. 48, No. 6, 591-596 (1977).

Zhai, et al.; "Recent Advances of High-pressure Generation in a Multianvil Apparatus Using Sintered Diamond Anvils"; Geoscience Frontiers 2(1) (2011) 101-106.

Wang; Acta Physica Sinica; vol. 59, No. 5, 181-189 (2010).

* cited by examiner

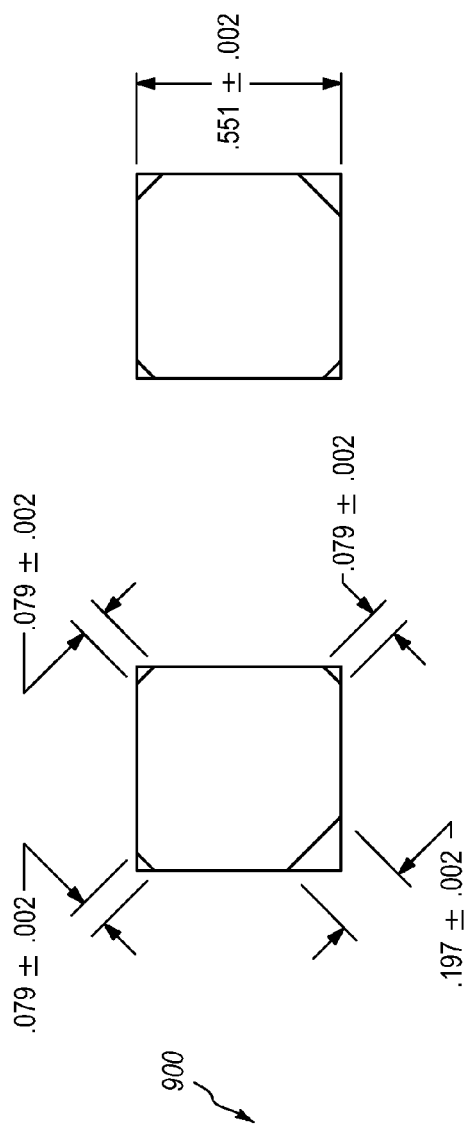
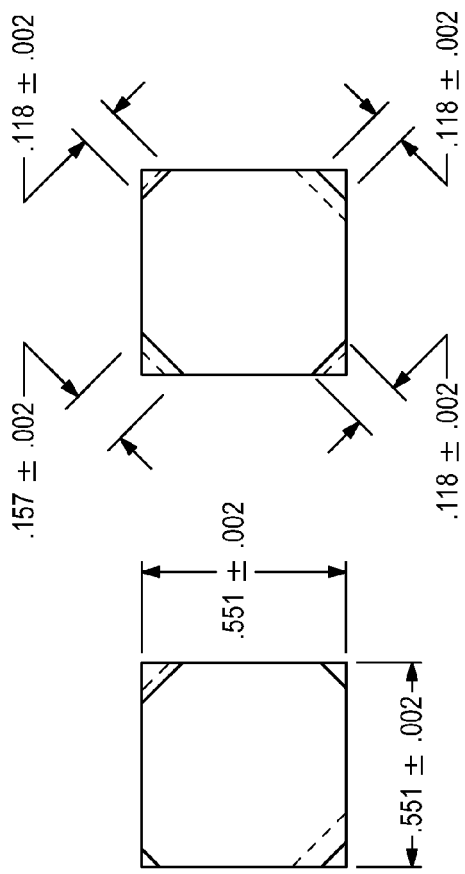
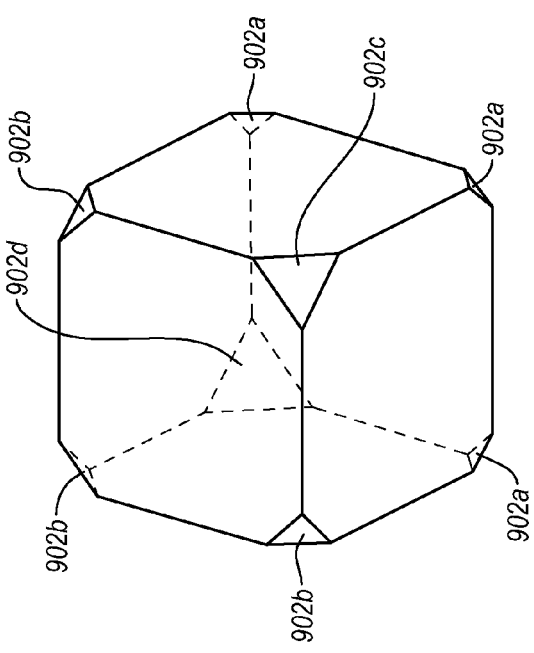
Fig. 9C
Fig. 9E
Fig. 9B
Fig. 9D
Fig. 9A

ANVILS AND ULTRA-HIGH PRESSURE APPARATUSES USING THE SAME

CROSS REFERENCE TO RELATED APPLICATIONS

This application claims priority to U.S. Patent Application No. 61/468,476 filed 28 Mar. 2011, the disclosure of which is incorporated herein, in its entirety, by this reference.

BACKGROUND

Various high-pressure/high-temperature ("HPHT") anvils are employed in HPHT presses. Existing anvil configurations are typically formed of tungsten carbide, and are operable up to pressures in the kilobar range (e.g., 10 kbar=1 GPa). Tungsten carbide exhibits lower than desirable hardness and relatively low transverse rupture strength, such that anvils formed of tungsten carbide are subject to plastic deformation, catastrophic tensile failure, or both, particularly at pressures over about 10 GPa.

Anvils may alternatively be formed from a single-crystal diamond material. Such anvils allow for operation at significantly higher pressures, although such single-crystal diamond anvils also suffer from a tendency to cleave along certain crystal planes. In addition, such single-crystal diamond anvils are mounted within a tungsten carbide seat, which tends to suffer from plastic deformation, as it is unable to provide sufficient support for the back portion of the single-crystal diamond anvil.

SUMMARY

Embodiments of the invention relate to polycrystalline diamond ("PCD") anvils for use in ultra-high pressure apparatuses and ultra-high pressure apparatuses using such PCD anvils. The PCD anvils disclosed herein enable applying enhanced pressure to a sample being analyzed while being sufficiently low in metal-solvent catalyst concentration to provide sufficient x-ray transparency for studying and analyzing the sample with x-rays, such as through x-ray diffraction.

In an embodiment, a PCD anvil includes an anvil body comprising PCD exhibiting enhanced diamond-to-diamond bonding and low metal-solvent catalyst concentration. The PCD includes a plurality of diamond grains defining a plurality of interstitial regions. A metal-solvent catalyst occupies at least a portion of the plurality of interstitial regions. The plurality of diamond grains and the metal-solvent catalyst collectively may exhibit a coercivity of about 115 Oe or more and a specific magnetic saturation of about 15 G·cm$^3$/g or less.

In an embodiment, the PCD anvil is formed from a polycrystalline diamond compact ("PDC"). The PCD anvil includes a PCD table bonded to a substrate. At least a portion of the PCD table may comprise PCD. The PCD includes a plurality of diamond grains defining a plurality of interstitial regions. A metal-solvent catalyst occupies at least a portion of the plurality of interstitial regions. The plurality of diamond grains and the metal-solvent catalyst collectively may exhibit a coercivity of about 115 Oe or more and a specific magnetic saturation of about 15 G·cm$^3$/g or less.

In some embodiments, the metal-solvent catalyst content present in the PCD may be about 7.5 weight % ("wt %") or less, even when un-leached. In an embodiment, such low metal-solvent catalyst content (even without leaching) may be achieved at least partially by employing ultra-high pressures during sintering of the diamond particles. For example, the cell pressure applied during HPHT processing may be at least about 7.5 GPa.

Further embodiments are directed to ultra-high pressure apparatuses that include one or more PCD anvils configured according to any of the PCD anvils disclosed herein. For example, the ultra-high pressure apparatuses may be configured as a diamond anvil cell in which single-crystal diamond anvils are replaced with any of the PCD anvils disclosed herein, a cubic anvil cell in which one or more of the anvils are configured according to any of the PCD anvils disclosed herein, or so-called "6-8" two-stage anvil cells in which both the first and second stage anvils may be configured according to any of the PCD anvils disclosed herein.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the invention, wherein identical reference numerals refer to identical or similar elements or features in different views or embodiments shown in the drawings.

FIGS. 9A-9E are different views of an embodiment of a second-stage PCD anvil.

DETAILED DESCRIPTION

I. Introduction

Figure 1A:
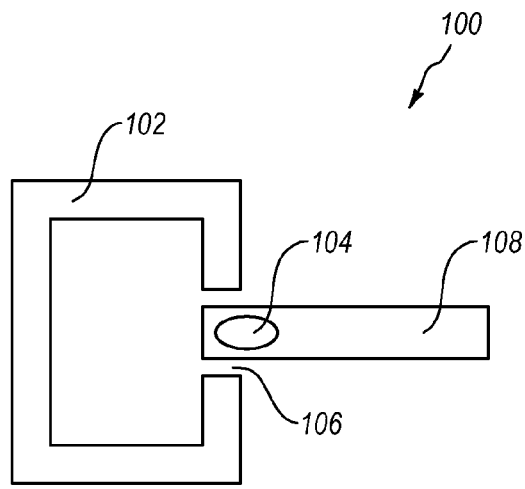
FIG. 1A is a schematic diagram of an example of a magnetic saturation apparatus configured to magnetize a PCD sample approximately to saturation.

Embodiments of the invention relate to PCD anvils for use in ultra-high pressure apparatuses and ultra-high pressure apparatuses using such PCD anvils. The PCD anvils disclosed herein enable applying enhanced pressure to a sample being analyzed while the PCD anvil is also sufficiently low in metal-solvent catalyst concentration to provide sufficient x-ray transparency for studying and analyzing the sample with x-rays such as by x-ray diffraction techniques. For example, high-pressure studies of minerals or other materials may be performed to simulate geologic environments. It is currently believed that as the sintering cell pressure employed during the HPHT process used to fabricate such PCD is moved further into the diamond-stable region away from the graphite-diamond equilibrium line, the rate of nucleation and growth of diamond increases. Such increased nucleation and growth of diamond between diamond particles (for a given diamond particle formulation) may allow PCD formation at a relatively lower metal-solvent catalyst concentration, a higher coercivity, a lower specific magnetic saturation, and/or a lower specific permeability (i.e., the ratio of specific magnetic saturation to coercivity) than PCD formed at a lower sintering pressure.

II. Embodiments of PCD Anvils

According to various embodiments, PCD anvils include a PCD body comprising PCD comprising a plurality of diamond grains directly bonded together via diamond-to-diamond bonding (e.g., $sp^3$ bonding) to define a plurality of interstitial regions therebetween. At least a portion of the interstitial regions or, in some embodiments, substantially all of the interstitial regions may be occupied by a metal-solvent catalyst, such as iron, nickel, cobalt, combinations thereof, or alloys of any of the foregoing metals. The plurality and diamond grains and metal-solvent catalyst collectively exhibit a coercivity of about 115 Oe or more, and a specific magnetic saturation of about 15 G·cm$^3$/g or less. In an embodiment, the PCD is formed by sintering at a cell pressure of at least about 7.5 GPa. In an embodiment, the metal-solvent catalyst content within the PCD may be about 7.5 wt % or less.

In an embodiment, the diamond grains may exhibit an average grain size of about 50 μm or less, such as about 30 μm or less or about 20 μm or less. For example, the average grain size of the diamond grains may be about 10 μm to about 18 μm and, in some embodiments, about 15 μm to about 25 μm, or about 15 μm to about 18 μm. In some embodiments, the average grain size of the diamond grains may be about 10 μm or less, such as about 2 μm to about 5 μm or submicron.

Furthermore, the diamond particle size distribution used in forming the PCD may exhibit a single mode, or may be a bimodal or greater grain size distribution (e.g., a trimodal diamond particle size distribution). In an embodiment, the diamond particles of the one or more layers of diamond particles may comprise a relatively larger size and at least one relatively smaller size. As used herein, the phrases "relatively larger" and "relatively smaller" refer to particle sizes (by any suitable method) that differ by at least a factor of two (e.g., 30 μm and 15 μm). According to various embodiments, the diamond particles may include a portion exhibiting a relatively larger average particle size (e.g., 50 μm, 40 μm, 30 μm, 20 μm, 15 μm, 12 μm, 10 μm, 8 μm) and another portion exhibiting at least one relatively smaller average particle size (e.g., 6 μm, 5 μm, 4 μm, 3 μm, 2 μm, 1 μm, 0.5 μm, less than 0.5 μm, 0.1 μm, less than 0.1 μm). In an embodiment, the diamond particles may include a portion exhibiting a relatively larger average particle size between about 10 μm and about 40 μm and another portion exhibiting a relatively smaller average particle size between about 1 μm and 4 μm. In some embodiments, the diamond particles may comprise three or more different average particle sizes (e.g., one relatively larger average particle size and two or more relatively smaller average particle sizes), without limitation.

It is noted that the as-sintered diamond grain size may differ from the average particle size of the mass of diamond particles prior to sintering due to a variety of different physical processes, such as grain growth, diamond particles fracturing, carbon provided from another carbon source (e.g., dissolved carbon in the metal-solvent catalyst), or combinations of the foregoing. The metal-solvent catalyst (e.g., iron, nickel, cobalt, or alloys thereof) may be provided in particulate form mixed with the diamond particles, as a thin foil or plate placed adjacent to the mass of diamond particles, from a cemented carbide substrate including a metal-solvent catalyst, or combinations of the foregoing.

In an embodiment, the metal-solvent catalyst that occupies at least a portion of the interstitial regions may be present in the PCD in an amount of about 7.5 wt % or less. In some embodiments, the metal-solvent catalyst may be present in the PCD in an amount of about 1 wt % to about 7.5 wt %, such as about 3 wt % to about 7.5 wt %, about 1 wt % to about 6 wt % or about 3 wt % to about 6 wt %. In other embodiments, the metal-solvent catalyst content may be present in the PCD in an amount of less than about 3 wt %, such as about 1 wt % to about 3 wt % or a residual amount to about 1 wt %. By maintaining the metal-solvent catalyst content below about 7.5 wt %, the PCD may be sufficiently transmissive to x-rays or other suitable radiation so that analysis of a sample being compressed can be performed, such as by x-ray diffraction.

Many physical characteristics of the PCD may be determined by measuring certain magnetic properties of the PCD because the metal-solvent catalyst may be ferromagnetic. The amount of the metal-solvent catalyst present in the PCD may be correlated with the measured specific magnetic saturation of the PCD. A relatively larger specific magnetic saturation indicates relatively more metal-solvent catalyst in the PCD.

The mean free path between neighboring diamond grains of the PCD may be correlated with the measured coercivity of the PCD. A relatively large coercivity indicates a relatively smaller mean free path. The mean free path is representative of the average distance between neighboring diamond grains of the PCD, and thus may be indicative of the extent of diamond-to-diamond bonding in the PCD. A relatively smaller mean free path, in well-sintered PCD, may indicate relatively more diamond-to-diamond bonding.

As merely one example, ASTM B886-03 (2008) provides a suitable standard for measuring the specific magnetic saturation and ASTM B887-03 (2008) el provides a suitable standard for measuring the coercivity of the PCD. Although both ASTM B886-03 (2008) and ASTM B887-03 (2008) el are directed to standards for measuring magnetic properties of cemented carbide materials, either standard may be used to determine the magnetic properties of PCD. A KOERZIMAT CS 1.096 instrument (commercially available from Foerster Instruments of Pittsburgh, Pa.) is one suitable instrument that may be used to measure the specific magnetic saturation and the coercivity of the PCD.

Generally, as the sintering cell pressure that is used to form the PCD increases, the coercivity may increase and the magnetic saturation may decrease. The PCD defined collectively by the bonded diamond grains and the metal-solvent catalyst may exhibit a coercivity of about 115 Oe or more and a specific magnetic saturation of about 15 G·cm³/g or less. Specific magnetic saturation of about 15 G·cm³/g or less may correlate to a metal-solvent catalyst concentration of less than about 7.5 wt %. In an embodiment, the coercivity of the PCD may be about 115 Oe to about 250 Oe and the specific magnetic saturation of the PCD may be greater than 0 G·cm³/g to about 15 G·cm³/g. In another embodiment, the coercivity of the PCD may be about 115 Oe to about 175 Oe and the specific magnetic saturation of the PCD may be about 5 G·cm³/g to about 15 G·cm³/g. In yet another embodiment, the coercivity of the PCD may be about 155 Oe to about 175 Oe and the specific magnetic saturation of the PCD may be about 10 G·cm³/g to about 15 G·cm³/g. The specific permeability (i.e., the ratio of specific magnetic saturation to coercivity) of the PCD may be about 0.10 or less, such as about 0.060 to about 0.090. Despite the average grain size of the bonded diamond grains being less than about 30 µm, the metal-solvent catalyst content in the PCD may be less than about 7.5 wt % resulting in a desirable thermal stability.

The temperature of the HPHT process may typically be at least about 1000° C. (e.g., about 1100° C. to about 2200° C., or about 1200° C. to about 1450° C.) and a cell pressure in the pressure transmitting medium of at least about 7.5 GPa (e.g., about 7.5 GPa to about 15 GPa) for a time sufficient to sinter the diamond particles together in the presence of the metal-solvent catalyst and form the PCD comprising bonded diamond grains defining interstitial regions occupied by the metal-solvent catalyst. For example, the cell pressure in the pressure transmitting medium employed in the HPHT process may be at least about 8.0 GPa, at least about 9.0 GPa, at least about 10.0 GPa, at least about 11.0 GPa, at least about 12.0 GPa, or at least about 14 GPa.

In an embodiment, diamond particles having an average particle size of about 18 µm to about 20 µm are positioned adjacent to a cobalt-cemented tungsten carbide substrate and subjected to an HPHT process at a temperature of about 1390° C. to about 1430° C. and a cell pressure of about 7.8 GPa to about 8.5 GPa. The PCD so-formed as a PCD table bonded to the substrate may exhibit a coercivity of about 155 Oe to about 175 Oe, a specific magnetic saturation of about 10 G·cm³/g to about 15 G·cm³/g, and a cobalt content of about 5 wt % to about 7.5 wt %.

In one or more embodiments, a specific magnetic saturation constant for the metal-solvent catalyst in the PCD may be about 185 G·cm³/g to about 215 G·cm³/g. For example, the specific magnetic saturation constant for the metal-solvent catalyst in the PCD may be about 195 G·cm³/g to about 205 G·cm³/g. It is noted that the specific magnetic saturation constant for the metal-solvent catalyst in the PCD may be composition dependent. For example, where the metal-solvent catalyst comprises nickel or iron, the specific magnetic saturation constant may be different than where the metal-solvent catalyst comprises cobalt.

PCD formed by sintering diamond particles having the same diamond particle size distribution as described above, but sintered at a relatively lower cell pressure of, for example, up to about 5.5 GPa and at temperatures in which diamond is stable may exhibit a coercivity of about 100 Oe or less and/or a specific magnetic saturation of about 16 G·cm³/g or more. Thus, in one or more embodiments of the invention, PCD exhibits a metal-solvent catalyst content of less than 7.5 wt % and a greater amount of diamond-to-diamond bonding between diamond grains than that of a PCD sintered at a lower cell pressure, but with all else being equal, e.g., the same precursor diamond particle size distribution and catalyst.

It is currently believed by the inventors that forming the PCD by sintering diamond particles at a cell pressure of at least about 7.5 GPa may promote nucleation and growth of diamond between the diamond particles being sintered so that the volume of the interstitial regions of the PCD so-formed is decreased compared to the volume of interstitial regions if the same diamond particle distribution was sintered at a cell pressure of, for example, up to about 5.5 GPa and at temperatures where diamond is stable. For example, the diamond may nucleate and grow from carbon provided by dissolved carbon in metal-solvent catalyst (e.g., liquefied cobalt) infiltrating into the diamond particles being sintered, partially graphitized diamond particles, carbon from a substrate, carbon from another source (e.g., graphite particles and/or fullerenes mixed with the diamond particles), or combinations of the foregoing. This nucleation and growth of diamond in combination with the sintering cell pressure of at least about 7.5 GPa and resulting relatively low volume of interstitial regions may contribute to PCD so-formed having a metal-solvent catalyst content of less than about 7.5 wt %.

Figure 1B:
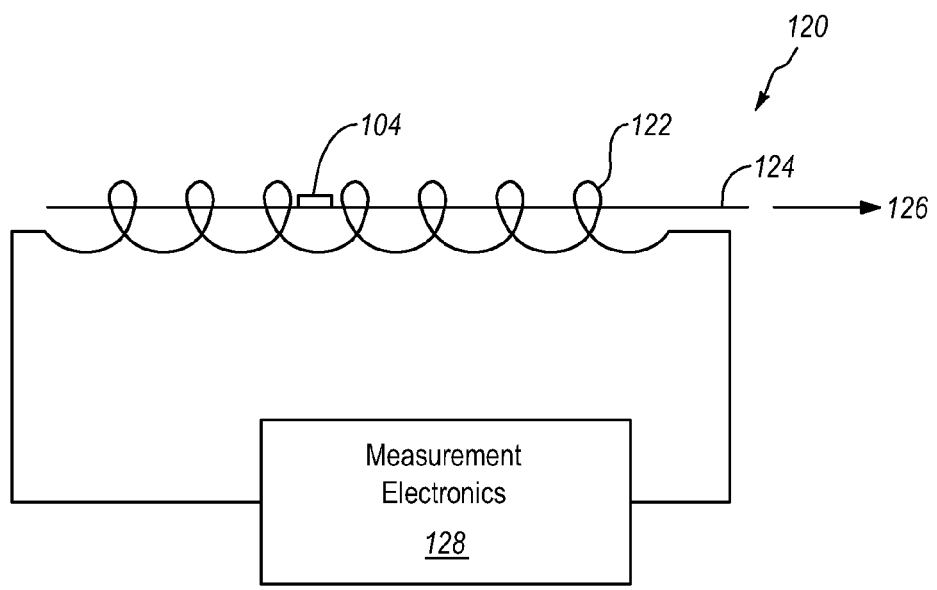
FIG. 1B is a schematic diagram of an example of a magnetic saturation measurement apparatus configured to measure a saturation magnetization of a PCD sample.
Figure 2:
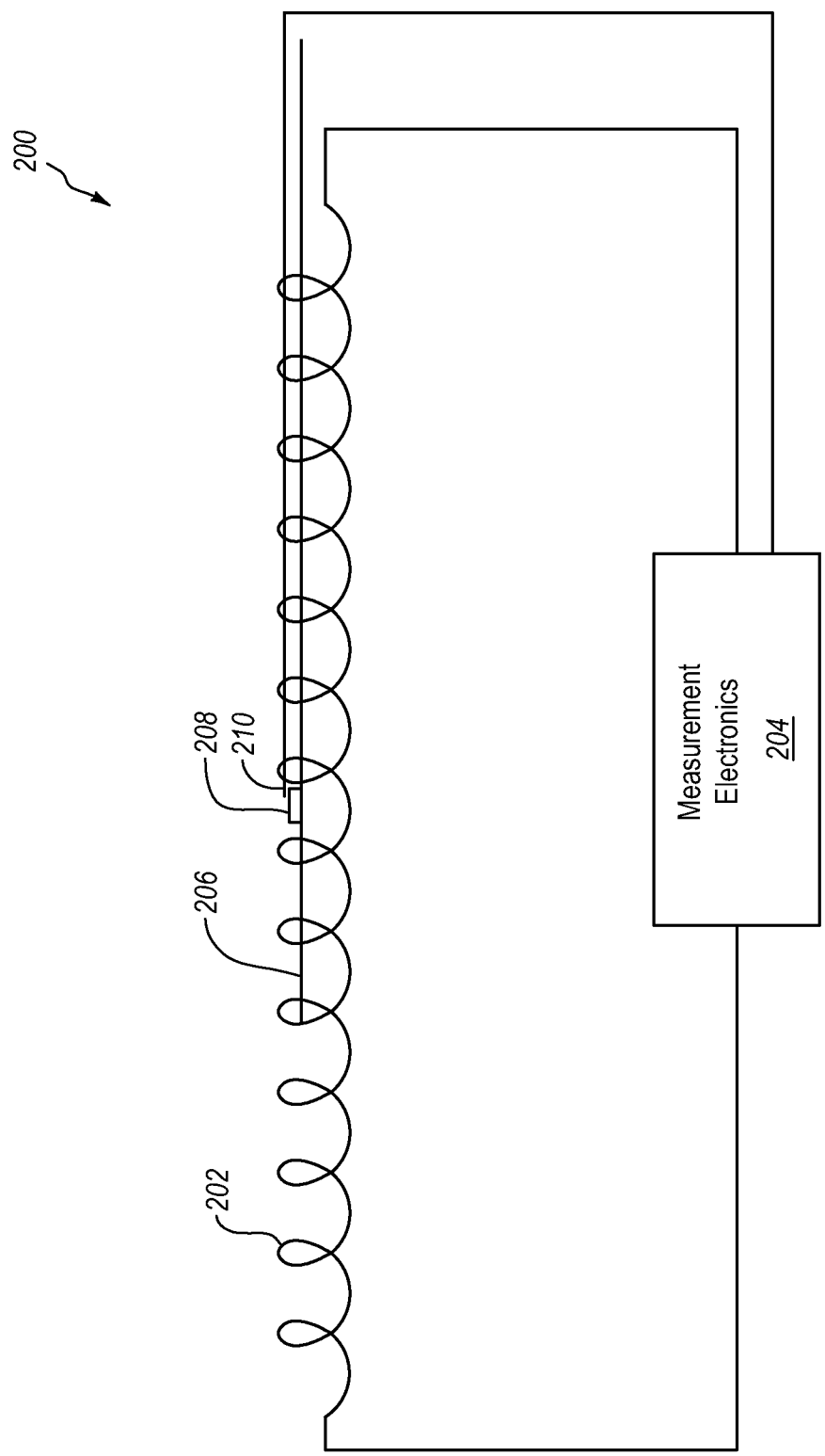
FIG. 2 is a schematic diagram of an example of a coercivity measurement apparatus configured to determine a coercivity of a PCD sample.

FIGS. 1A, 1B, and 2 schematically illustrate the manner in which the specific magnetic saturation and the coercivity of the PCD may be determined using an apparatus, such as the KOERZIMAT CS 1.096 instrument. FIG. 1A is a schematic diagram of an example of a magnetic saturation apparatus 100 configured to magnetize a PCD sample to saturation. The magnetic saturation apparatus 100 includes a saturation magnet 102 of sufficient strength to magnetize a PCD sample 104 to saturation. The saturation magnet 102 may be a permanent magnet or an electromagnet. In the illustrated embodiment, the saturation magnet 102 is a permanent magnet that defines an air gap 106, and the PCD sample 104 may be positioned on a sample holder 108 at least partially inserted within the air gap 106. When the PCD sample 104 is light-weight, it may be secured to the sample holder 108 using, for example, double-sided tape or other adhesive so that the PCD sample 104 does not move responsive to the magnetic field from the saturation magnet 102 and the PCD sample 104 is magnetized approximately to saturation.

Referring to the schematic diagram of FIG. 1B, after magnetizing the PCD sample 104 approximately to saturation using the magnetic saturation apparatus 100, a magnetic saturation of the PCD sample 104 may be measured using a magnetic saturation measurement apparatus 120. The magnetic saturation measurement apparatus 120 may include a Helmholtz measuring coil 122 defining a passageway dimensioned so that the magnetized PCD sample 104 may be positioned therein on a sample holder 124. Once positioned in the passageway, the sample holder 124 supporting the magnetized PCD sample 104 may be moved axially along an axis direction 126 to induce a current in the Helmholtz measuring coil 122. Measurement electronics 128 are coupled to the Helmholtz measuring coil 122 and configured to calculate the magnetic saturation based upon the measured current passing through the Helmholtz measuring coil 122. The measurement electronics 128 may also be configured to calculate a weight percentage of magnetic material in the PCD sample 104 when the composition and magnetic characteristics of the metal-solvent catalyst in the PCD sample 104 are known, such as with iron, nickel, cobalt, and alloys thereof. Specific magnetic saturation may be calculated based upon the calculated magnetic saturation and the measured weight of the PCD sample 104.

The amount of metal-solvent catalyst in the PCD sample 104 may be determined using a number of different analytical techniques. For example, energy dispersive spectroscopy (e.g., EDAX), wavelength dispersive x-ray spectroscopy (e.g., WDX), and/or Rutherford backscattering spectroscopy may be employed to determine the amount of metal-solvent catalyst in the PCD sample 104.

If desired, a specific magnetic saturation constant of the metal-solvent catalyst in the PCD sample 104 may be determined using an iterative approach. A value for the specific magnetic saturation constant of the metal-solvent catalyst in the PCD sample 104 may be iteratively chosen until a metal-solvent catalyst content calculated by the analysis software of the KOERZIMAT CS 1.096 instrument using the chosen value substantially matches the metal-solvent catalyst content determined via an analytical technique, such as energy dispersive spectroscopy, wavelength dispersive x-ray spectroscopy, and/or Rutherford backscattering spectroscopy.

FIG. 2 is a schematic diagram of a coercivity measurement apparatus 200 configured to determine a coercivity of a PCD sample. The coercivity measurement apparatus 200 includes a coil 202 and measurement electronics 204 coupled to the coil 202. The measurement electronics 204 are configured to pass a current through the coil 202 so that a magnetic field is generated. A sample holder 206 having a PCD sample 208 thereon may be positioned within the coil 202. A magnetization sensor 210 configured to measure a magnetization of the PCD sample 208 may be coupled to the measurement electronics 204 and positioned in proximity to the PCD sample 208.

During testing, the magnetic field generated by the coil 202 magnetizes the PCD sample 208 approximately to saturation. Then, the measurement electronics 204 apply a current so that the magnetic field generated by the coil 202 is increasingly reversed. The magnetization sensor 210 measures a magnetization of the PCD sample 208 resulting from application of the reversed magnetic field to the PCD sample 208. The measurement electronics 204 determine the coercivity of the PCD sample 208, which is a measurement of the reverse magnetic field at which the magnetization of the PCD sample 208 is zero.

In order to efficiently sinter the mass of diamond particles, the mass may be enclosed in a pressure transmitting medium, such as a refractory metal can, graphite structure, pyrophyllite, and/or other suitable pressure transmitting structure to form a cell assembly. Examples of suitable gasket materials and cell structures for use in manufacturing PCD are disclosed in U.S. Pat. No. 6,338,754 and U.S. patent application Ser. No. 11/545,929, each of which is incorporated herein, in its entirety, by this reference. Another example of a suitable pressure transmitting material is pyrophyllite, which is commercially available from Wonderstone Ltd. of South Africa. The cell assembly, including the pressure transmitting medium and mass of diamond particles therein, is subjected to an HPHT process using an ultra-high pressure press, for example, at temperatures (e.g., at least about 1000° C.) and cell pressures (e.g., at least about 7.5 GPa) as described above.

Any pressure values employed in the HPHT processes disclosed herein refer to the pressure in the pressure transmitting medium at room temperature (e.g., about 25° C.) with application of pressure using an ultra-high pressure press and not the pressure applied to the exterior of the cell assembly. The actual pressure in the pressure transmitting medium at sintering temperature may be slightly higher than that at room temperature.

In an embodiment, a cell pressure of at least about 7.5 GPa in the pressure transmitting medium may be generated by applying pressure to a cubic high-pressure cell assembly that encloses the mass of diamond particles to be sintered using anvils, with each anvil applying pressure to a different face of the cubic high-pressure assembly. In such an embodiment, a surface area of each anvil face of the anvils may be selectively dimensioned to facilitate application of cell pressure of at least about 7.5 GPa to the mass of diamond particles being sintered. For example, the surface area of each anvil may be less than about 12.0 cm$^2$, such as about 8 cm$^2$ to about 10 cm$^2$. The anvils may be made from a cobalt-cemented tungsten carbide, single-crystal diamond, PCD as disclosed herein, or other material having a sufficient compressive strength to help reduce damage thereto through repetitive use in a high-volume commercial manufacturing environment. Optionally, as an alternative to or in addition to selectively dimensioning the surface area of each anvil face, two or more internal anvils may be embedded in the cubic high-pressure cell assembly to further intensify pressure. For example, the article W. Utsumi, N. Toyama, S. Endo and F. E. Fujita, "X-ray diffraction under ultrahigh pressure generated with sintered diamond anvils," J. Appl. Phys., 60, 2201 (1986) is incorporated herein, in its entirety, by this reference and discloses that sintered diamond anvils may be embedded in a cubic pressure transmitting medium for intensifying the cell pressure applied by an ultra-high pressure press to a workpiece also embedded in the cubic pressure transmitting medium.

Figure 3:
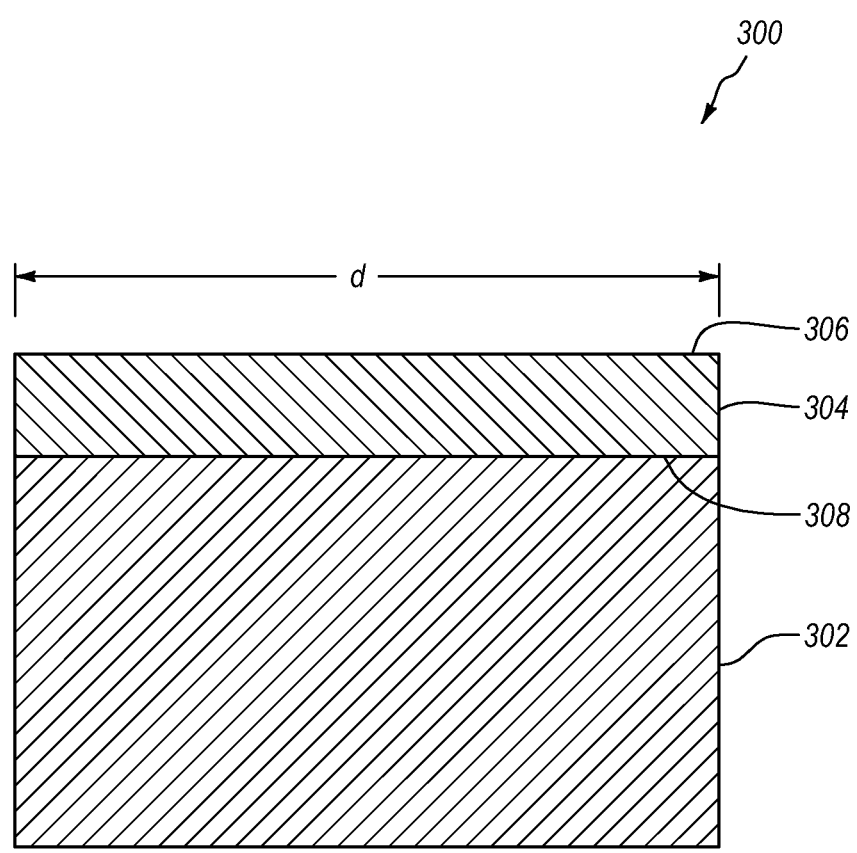
FIG. 3 is a cross-sectional view of an embodiment of a PDC including a PCD table formed from any of the PCD embodiments disclosed herein.

Referring to FIG. 3, the PCD embodiments may be employed in a PDC for use as an anvil in an ultra-high pressure apparatus. FIG. 3 is a cross-sectional view of an embodiment of a PDC 300. The PDC 300 includes a substrate 302 bonded to a PCD table 304. The PCD table 304 may be formed of PCD in accordance with any of the PCD embodiments disclosed herein. The PCD table 304 exhibits an anvil face 306 and at least one lateral dimension "d" (e.g., a diameter). The substrate 302 may be generally cylindrical or another selected configuration, without limitation. Although FIG. 3 shows an interfacial surface 308 of the substrate 302 as being substantially planar, the interfacial surface 308 may exhibit a selected nonplanar topography, such as a grooved, ridged, or other nonplanar interfacial surface. The substrate 302 may comprise, without limitation, cemented carbides, such as tungsten carbide, titanium carbide, chromium carbide, niobium carbide, tantalum carbide, vanadium carbide, or combinations thereof cemented with iron, nickel, cobalt, or alloys thereof. For example, in an embodiment, the substrate 302 comprises cobalt-cemented tungsten carbide.

The PCD table 304 and, if desired, the substrate 302 may be shaped by grinding, electro-discharge machining, laser-shaping, combinations thereof, or another suitable material removal process to form a PCD anvil with a selectively tailored geometry. However, in other embodiments, the PCD anvils may be HPHT-processed to near net shape.

Additionally details about the composition, magnetic properties, and fabrication techniques for synthesizing PCD is disclosed in U.S. Pat. No. 7,866,418, the disclosure of which is incorporated herein, in its entirety, by this reference.

Figure 4A:
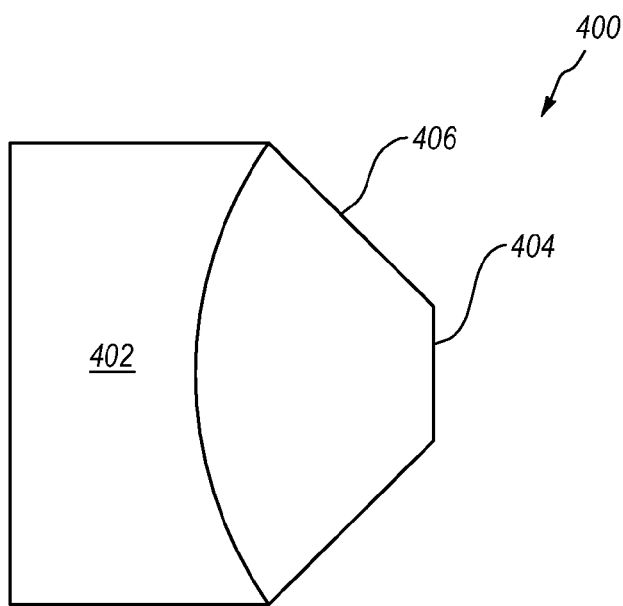
FIGS. 4A and 4B are side and top plan views, respectively, of an embodiment of a PCD anvil that does not include a substrate.
Figure 4B:
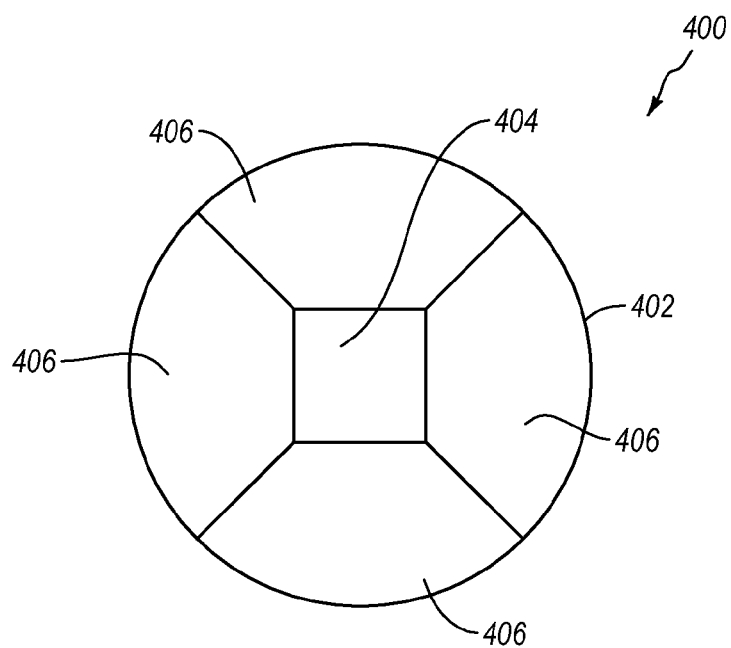
Figure 5A:
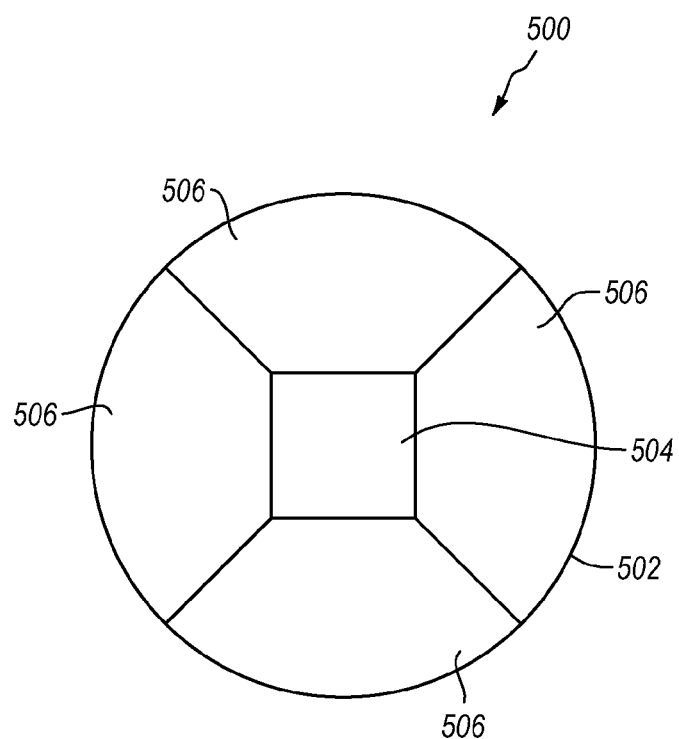
FIGS. 5A and 5B are side and top plan views, respectively, of another embodiment of a PCD anvil that includes a substrate to which the PCD anvil is attached.
Figure 5B:
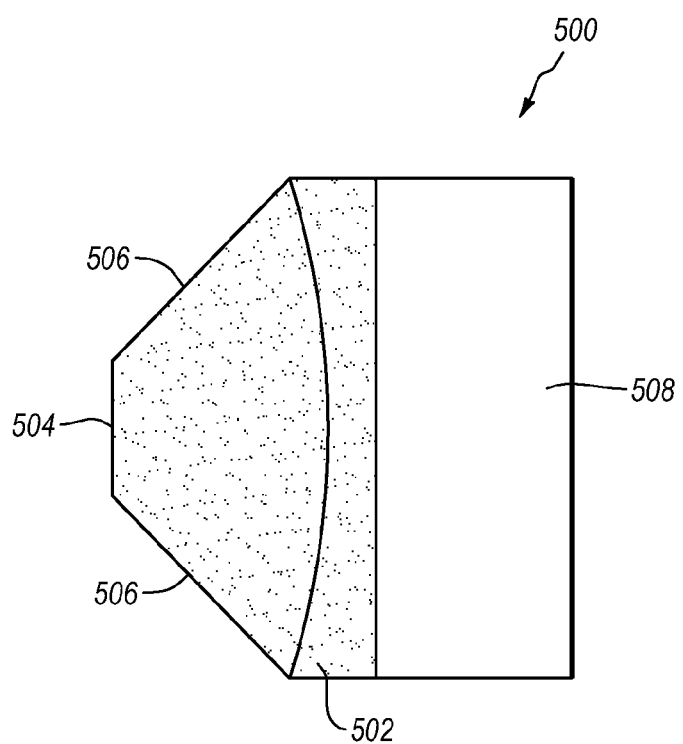

FIGS. 4A-9 illustrate various embodiments of selectively-shaped PCD anvils. FIGS. 4A and 4B illustrate an embodiment of a PCD anvil 400 that does not have a substrate. The PCD anvil 400 includes an anvil body 402 defining an anvil face 404. Anvil body 402 includes a chamfer surface 406 that may be angled at about 45° relative to anvil face 404. While illustrated with a chamfer angle of about 45°, it will be understood that in other embodiments, the angle may be more or less than 45°, such as about 30° to about 50°. FIGS. 5A and 5B illustrate an embodiment of a PCD anvil 500 including a selectively-shaped PCD table 502 defining an anvil face 504 that is bonded to a substrate 508. PCD table 502 is shown as including chamfer surfaces 506. PCD table 502 may have any desired thickness, for example, from about 0.05 inch to about 1 inch, from about 0.1 inch to about 0.5 inch, or from about 0.2 inch to about 0.4 inch.

Figure 6A:
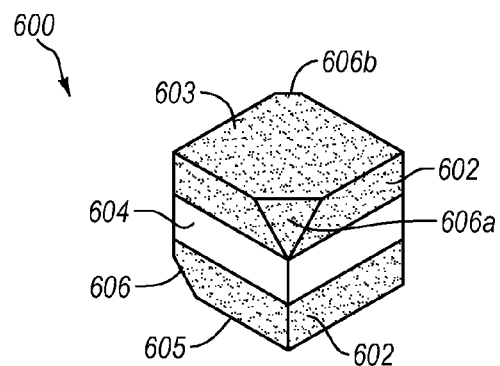
FIGS. 6A-6D are different views of an embodiment of a second-stage PCD anvil that includes a substrate and two opposing PCD tables.
Figure 6B:
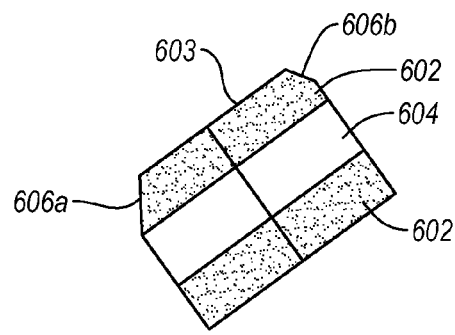
Figure 6C:
Figure 6D:
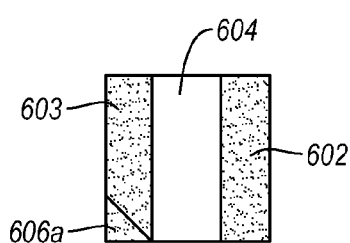

FIGS. 6A-6D illustrate an embodiment of a second-stage PCD anvil 600 for use in a so-called "6-8" ultra-high-pressure apparatus including selectively-shaped PCD tables 602 bonded to opposing sides of a substrate 604. As shown in FIGS. 6A-6D, one or more corners of each PCD table 602 adjacent exposed top face 603 or bottom face 605 may include a triangular cut 606. For example, in an embodiment, opposing corners of each PCD table 602 may include a triangular cut. PCD tables 602 may be formed from any of the PCD materials disclosed herein. The triangular cuts may be made at any desired angle. In an embodiment, the triangular cuts provide an angle between about 30° and about 40° (e.g., about 35°) relative to the adjacent exposed face of the PCD table 602. Each side of triangular cuts 606 may be substantially equal to one another for a given triangular cut (i.e., forming an equilateral triangle). As best seen in FIGS. 6A and 6B, in an embodiment, a surface area of triangular cut 606a may be larger than a surface area of triangular cut 606b (e.g., each side of triangular cut 606b may measure about half the value of triangular cut 606a).

Figure 7:
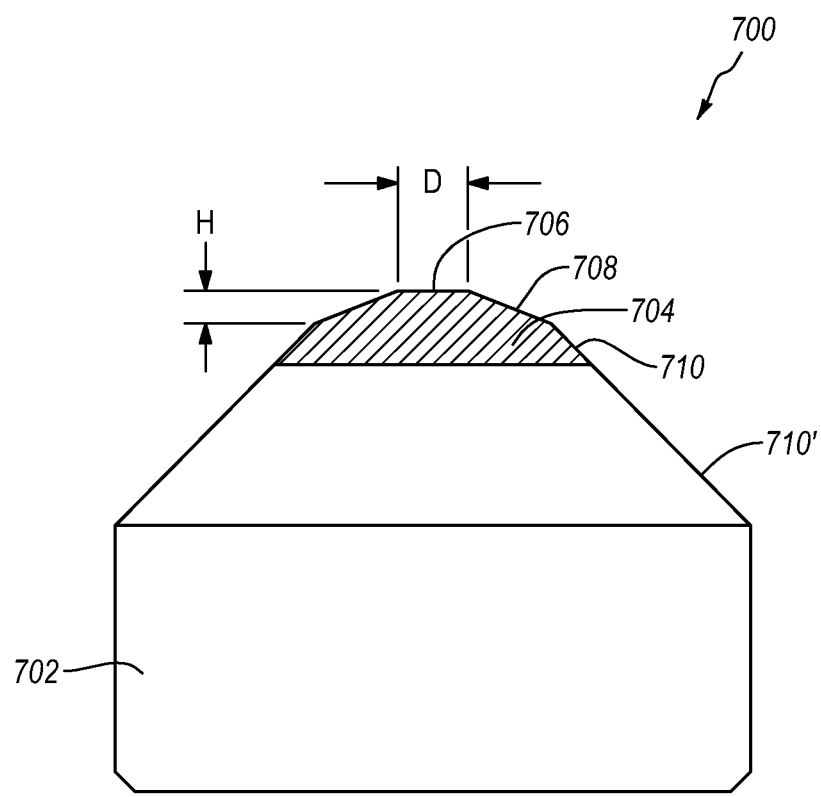
FIG. 7 is a side view of an embodiment of a PCD anvil for a diamond anvil cell.

FIG. 7 shows an embodiment of a PCD anvil 700 including a substrate 702 bonded to a PCD table 704 defining an anvil face 706. PCD table 704 includes two chamfer angles, with surface 708 being at an angle of about 5° to about 20° (e.g., about) 10° relative to anvil face 706, and surface 710 being at an angle of about 30° to about 60° (e.g., about 50°) relative to anvil face 706. The thickness of PCD table 704 may be about 0.05 inch to about 0.1 inch (e.g., about 0.079 inch). The total thickness of anvil 700 may be about 0.3 inch to about 0.5 inch (e.g., about 0.394 inch), and the bottom portion of substrate 702 (not bounded by 50° angled surface 710') may have a thickness from about 0.15 inch to about 0.3 inch (e.g., about 0.236 inch). The thickness H (corresponding to that portion of PCD table 704 bounded by the 10° angled surface) and anvil face 706 diameter D dimensions may be as shown below in Table I. In an embodiment, H may range from about 0.002 inch to about 0.04 inch. D may range from about 0.002 inch to about 0.3 inch.

TABLE I

| Anvil Face Diameter D (inch) | 10° Layer Thickness H (inch) |
|---|---|
| 0.197 | 0.004 |
| 0.118 | 0.012 |
| 0.039 | 0.020 |
| 0.020 | 0.022 |
| 0.012 | 0.023 |
| 0.004 | 0.024 |

Figure 8A:
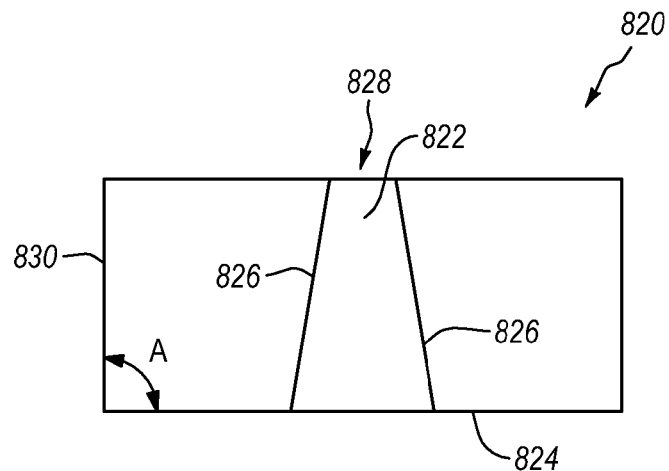
FIG. 8A is a side view of an embodiment of a seat for a PCD anvil.
Figure 8B:
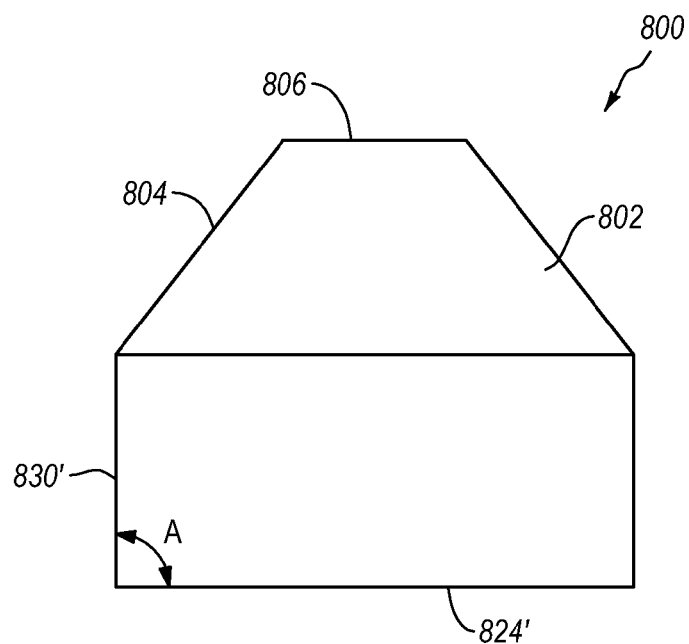
FIG. 8B is a side view of an embodiment of a PCD anvil for use with the seat shown in FIG. 8A.

FIGS. 8A and 8B illustrate an embodiment of a seat with an x-ray aperture 820 (FIG. 8A) and a corresponding PCD anvil 800 (FIG. 8B). PCD anvil 800 may include a PCD body 802, an anvil face 806, and a chamfered surface 804 (e.g., at about 45° relative to face 806). PCD anvil 800 comprises a plurality of bonded diamond grains with a relatively low concentration of metal-solvent catalyst occupying interstitial regions between the bonded diamond grains thereof. The PCD anvil 800 exhibits a coercivity of about 115 Oe or more and a specific magnetic saturation of about 15 G·cm$^3$/g or less, which advantageously provides sufficient x-ray transparency to allow study and analysis using x-ray analysis, such as through x-ray diffraction.

Corresponding seat 820 of FIG. 8B may comprise PCD or polycrystalline cubic boron nitride. Seat 820 includes an x-ray aperture 822 whose width may be flared so as to provide a width adjacent seating surface 824 that is greater than its width at an opposite end (i.e., inlet 828). For example, x-ray aperture may be flared at an angle from about 20° to about 40° (e.g., about 30°) between its bounding sidewalls 826. The width at inlet 828 may be from about 0.01 inch to about 0.03 inch (e.g., about 0.024 inch), the thickness of seat 820 from about 0.1 inch to about 0.3 inch (e.g., about 0.197 inch). An angle A between lateral sides 830 and seating surface 824 may provide an angle slightly less than 90° (e.g., between about 85° and less than 90°, or between about 87° and about 89°). PCD anvil 800 may have a width at its base 824' that is substantially equal to that of seating surface 824 of seat 820, while an angle A between lateral sides 830' and base 824' may be similarly angled at an angle slightly less than 90°.

FIGS. 9A-9E illustrate an embodiment of a second-stage PCD anvil 900 for use in a so-called "6-8" ultra-high-pressure apparatus including selectively shaped triangular corner faces 902a-902d with a plurality of different face sizes. Example face dimensions are shown in FIGS. 9B-9E. FIG. 9A includes like sized triangular corner faces labeled with like reference numbers (e.g., 3 triangular corner faces 902a are similarly sized, 2 faces 902b are similarly sized, one face each is sized as referenced by 902c and 902d, respectively). Although a substrate is not illustrated in the embodiment of FIGS. 9A-9E, in some embodiments, a substrate may be bonded to opposing PCD tables (e.g., similar to the embodiment shown in FIGS. 6A-6D) in which the corner faces 902a-902d are defined.

Figure 10:
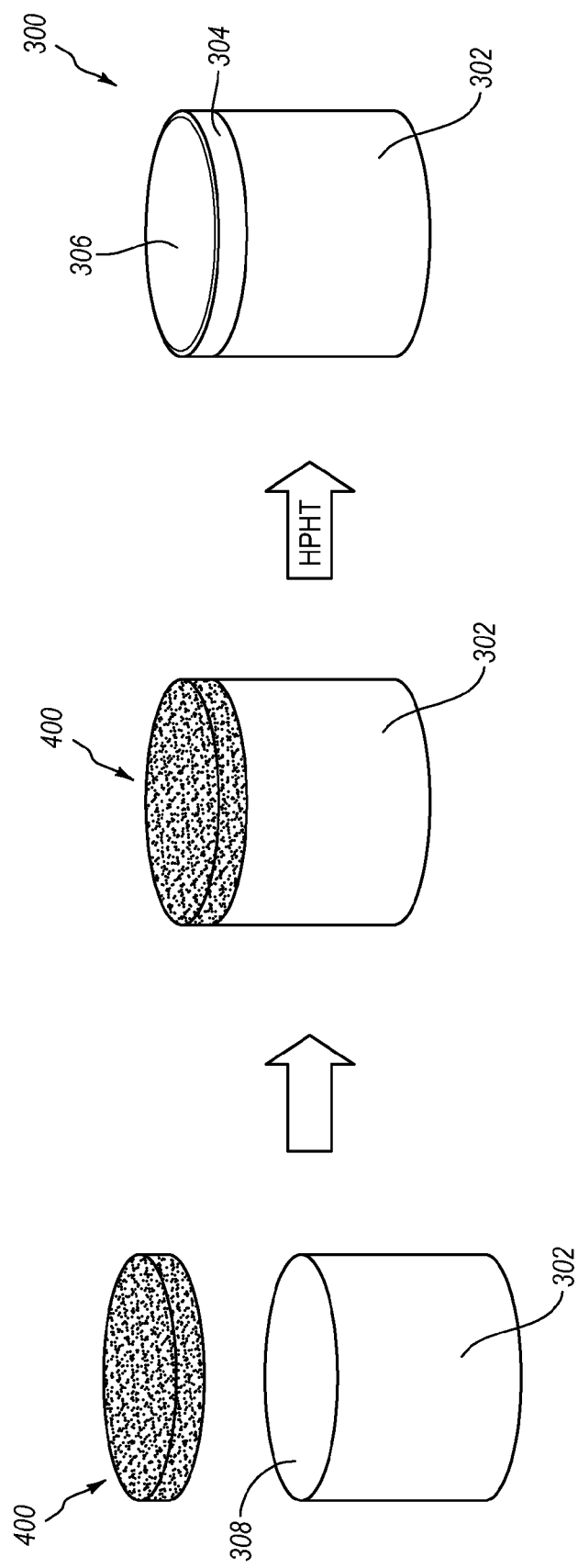
FIG. 10 is a schematic illustration of a method of fabricating the PDC shown in FIG. 3.

FIG. 10 is a schematic illustration of an embodiment of a method for fabricating the PDC 300 shown in FIG. 3. Such a PDC can be shaped to provide the desired PCD anvil. Referring to FIG. 10, a mass of diamond particles 400 having any of the above-mentioned average particle sizes and distributions (e.g., an average particle size of about 50 µm or less) is positioned adjacent to the interfacial surface 308 of substrate 302. As previously discussed, the substrate 302 may include a metal-solvent catalyst. The mass of diamond particles 400 and substrate 302 may be subjected to an HPHT process using conditions previously described with respect to sintering the PCD embodiments disclosed herein. The PDC 300 so-formed includes the PCD table 304 that comprises PCD, formed of any of the PCD embodiments disclosed herein, integrally formed with the substrate 302 and bonded to the interfacial surface 308 of the substrate 302. If the substrate 302 includes a metal-solvent catalyst, the metal-solvent catalyst may liquefy and infiltrate the mass of diamond particles 400 to promote growth between adjacent diamond particles of the mass of diamond particles 400 to form the PCD table 304 comprised of a body of bonded diamond grains having the infiltrated metal-solvent catalyst interstitially disposed between bonded diamond grains. For example, if the substrate 302 is a cobalt-cemented tungsten carbide substrate, cobalt from the substrate 302 may be liquefied and infiltrate the mass of diamond particles 400 to catalyze formation of the PCD table 304.

In any of the embodiments disclosed herein, substantially all or a selected portion of the metal-solvent catalyst may be removed (e.g., via leaching) from the PCD body or PCD table. In an embodiment, metal-solvent catalyst in the PCD body or PCD table may be removed to a selected depth from at least one exterior working surface (e.g., the working surface 306 and/or a sidewall working surface of the PCD table 304 or other anvil face in other embodiments) so that only a portion of the interstitial regions are occupied by metal-solvent catalyst. For example, substantially all or a selected portion of the metal-solvent catalyst may be removed from the PCD table 304 so-formed in the PDC 300 to a selected depth from the working surface 306. For example, the depth "d" may be about 50 μm to about 500 μm, about 200 μm to about 400 μm, about 300 μm to about 450 μm, or about 50 μm to about 100 μm. When leached, the metal-solvent catalyst may be present in the leached region in an amount of about 2 wt % or less, about 0.8 wt % to about 1.50 wt %, or about 0.86 wt % to about 1.47 wt %. By leaching, the ability of the PCD table 304 to allow x-rays to be transmitted therethrough may be further enhanced.

In another embodiment, a PCD table may be fabricated according to any of the disclosed embodiments in a first HPHT process, leached to remove substantially all of the metal-solvent catalyst from the interstitial regions between the bonded diamond grains, and subsequently bonded to a substrate in a second HPHT process. In the second HPHT process, an infiltrant from, for example, a cemented carbide substrate may infiltrate into the interstitial regions from which the metal-solvent catalyst was depleted. For example, the infiltrant may be cobalt that is swept-in from a cobalt-cemented tungsten carbide substrate. In an embodiment, the first and/or second HPHT process may be performed at a cell pressure of at least about 7.5 GPa. In an embodiment, the infiltrant may be leached from the infiltrated PCD table using a second acid leaching process following the second HPHT process.

III. Embodiments of Ultra-High Pressure Apparatuses Using PCD Anvils

Figure 11A:
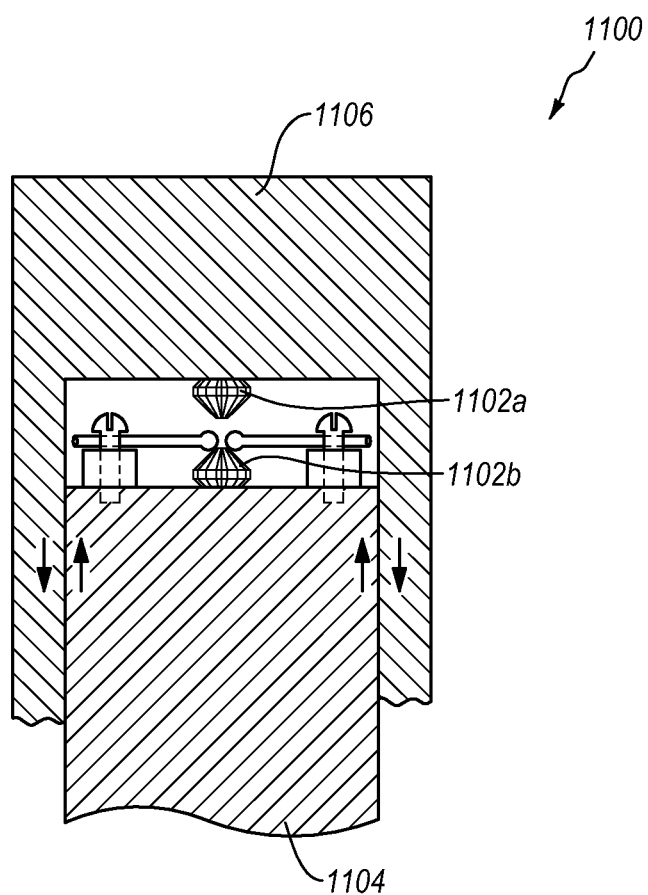
FIGS. 11A and 11B are side cross-sectional cutaway views of different embodiments of diamond anvil cells that may use a PCD anvil and/or seat as disclosed herein.

FIG. 11A is side cross-sectional cutaway view of an embodiment of a diamond anvil cell 1100 including two opposing PCD anvils 1102a and 1202b. PCD anvils 1102a and 1102b may be configured according to, for example, the PCD anvils shown in FIG. 4A-5B, 7, or 8B. In use, a sample may be compressed between PCD anvils 1102a and 1102b by applying a load to piston 1104 received within cylinder 1106. Piston 1104 compresses the sample between the PCD anvils 1102a and 1102b. X-ray diffraction may be performed on the sample during compression by irradiating the sample with x-rays from an x-ray diffractometer.

Figure 11B:
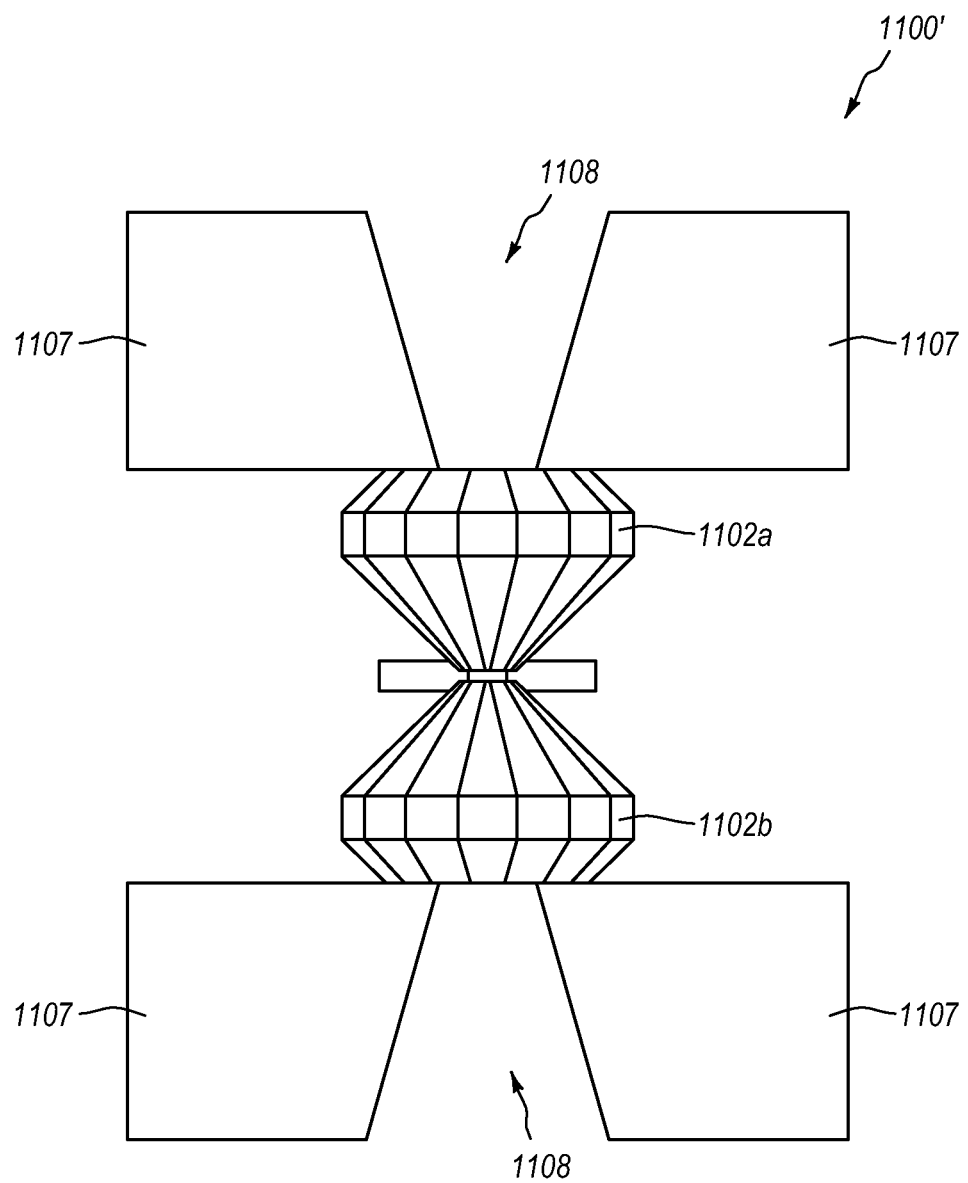

FIG. 11B is side cross-sectional cutaway view of another embodiment of an ultra-high pressure apparatus 1100' including two opposing PCD anvils 1102a and 1102b supported by superhard seats 1107 that each have an x-ray aperture 1108 formed therein. X-rays may be transmitted through the x-ray aperture 1008 and through the PCD anvils 1102a and 1102b to perform, for example, x-ray diffraction on a sample being compressed between the PCD anvils 1102a and 1102b.

Figure 12:
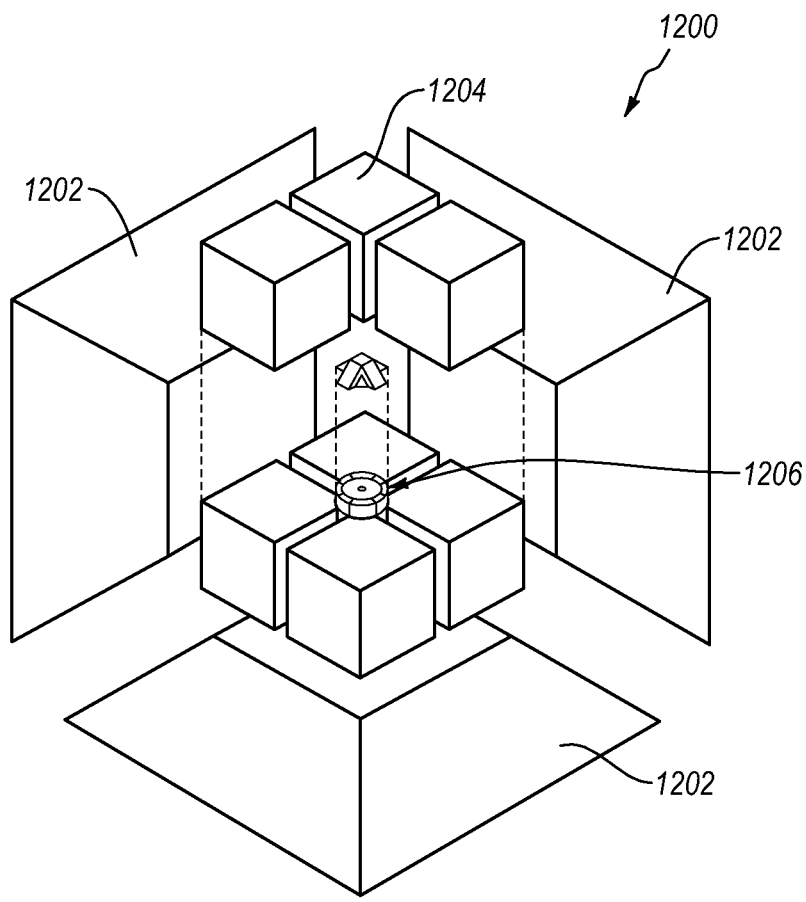
FIG. 12 is an exploded isometric view of an embodiment of a two-stage ultra-high pressure apparatus that may employ first- and second-stage PCD anvils as disclosed herein.

FIG. 12 is an exploded isometric-sectional view of an ultra-high pressure apparatus 1200 including six first-stage PCD anvils 1202 (only three shown) and eight second-stage anvils 1204 (only seven shown). The first stage PCD anvils 1202 may be configured according to, for example, the PCD anvils shown in FIG. 4A-5B, 7, or 8B. The second stage PCD anvils 1204 may be configured according to, for example, the PCD anvils shown in FIGS. 6A-6D, or FIGS. 9A-9E. The faces of the second-stage anvils 1204 are arranged to define an octahedral space in which a sample is placed within high-pressure cell 1206 and compressed by application of pressure to the second-stage anvils 1204 by the first stage PCD anvils 1202.

Figure 13:
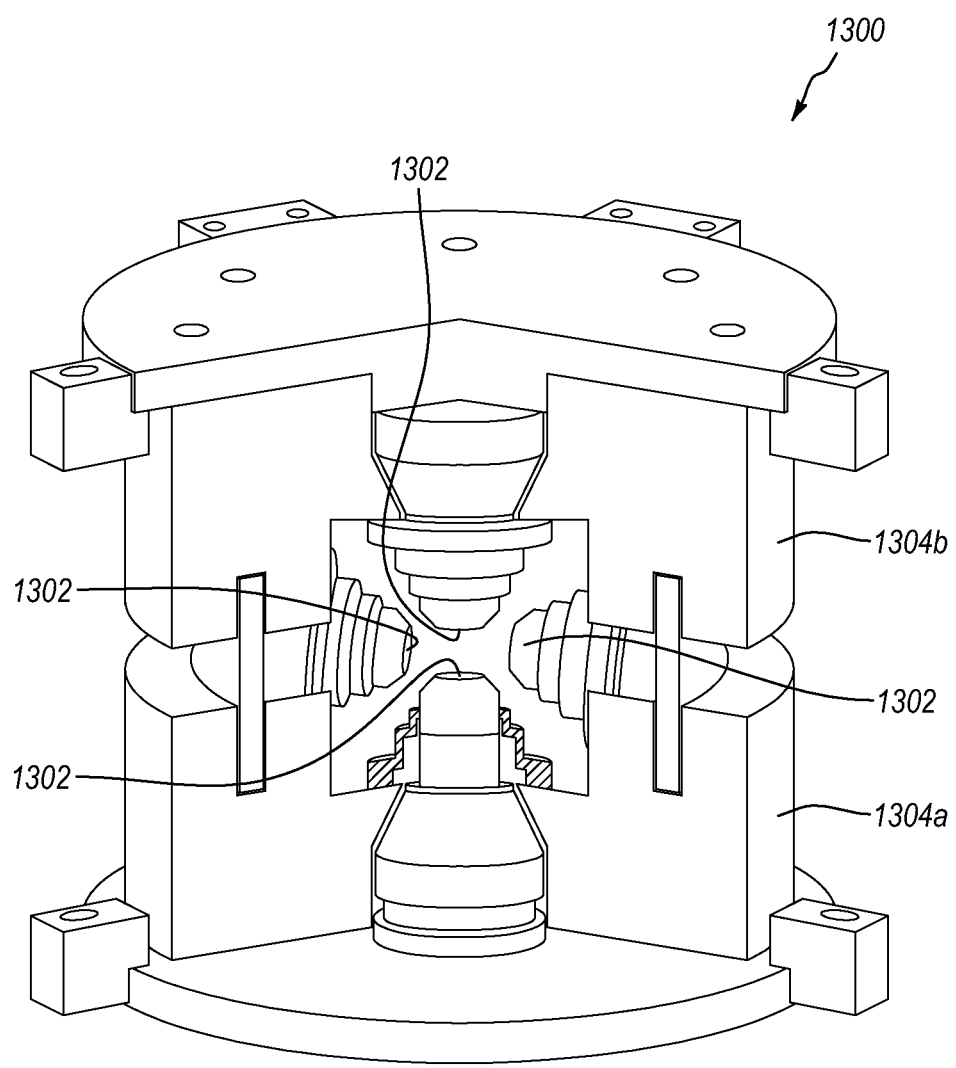
FIG. 13 is a cutaway isometric view of an embodiment of an ultra-high pressure apparatus that may employ PCD anvils as disclosed herein.

FIG. 13B is a cutaway isometric views of an embodiment of an ultra-high pressure apparatus 1300 that may employ PCD anvils 1302 as disclosed herein. Five of the PCD anvils 1302 may be disposed in a lower support plate 1304a and another one of the PCD anvils 1302 may be disposed in a moveable upper support plate 1304b. In operation, a hydraulic load is applied to the upper support plate 1304b to drive the PCD anvil 1302 supported therein to compress a sample disposed between the anvil faces of the PCD anvils 1302. X-rays may be transmitted through a conical or other shaped x-ray path to irradiate the sample being compressed by the PCD anvils 1302. X-rays received from the sample (e.g., diffracted or transmitted x-rays) may be received through a similar, oppositely disposed path.

In other embodiments, materials other than the low-metal-solvent catalyst PCD may be employed. For example, the anvils may be made from diamond-silicon carbide composites and superabrasive compacts including a diamond-silicon carbide composite table as disclosed in U.S. Pat. No. 7,998,573, the disclosure of which is incorporated herein, in its entirety, by this reference. In another embodiment, all of or a part of (e.g., the table) the anvils disclosed herein and/or seats disclosed herein may be made from polycrystalline cubic boron nitride.

All references cited herein and not already incorporated herein in their entirety are hereby incorporated herein, in their entirety, by this reference.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

The invention claimed is:

1. A polycrystalline diamond anvil for use in an ultra-high pressure apparatus, comprising:
   an anvil body defining an anvil face, the anvil body comprising:
      a plurality of bonded diamond grains directly bonded together and defining a plurality of interstitial regions, the plurality of bonded diamond grains having an average grain size of 30 μm or less;
      a metal-solvent catalyst occupying at least a portion of the plurality of interstitial regions, the metal-solvent catalyst present in a concentration from 1 weight % to 6 weight %;
      wherein the plurality of diamond grains and the metal-solvent catalyst collectively exhibit a coercivity from 115 Oe to 250 Oe; and
      wherein the plurality of diamond grains and the metal-solvent catalyst collectively exhibit a specific magnetic saturation of about 15 G·cm$^3$/g or less.

2. The polycrystalline diamond anvil of claim 1, wherein the concentration of the metal-solvent catalyst is 1 wt % to 3 wt %.

3. The polycrystalline diamond anvil of claim 1, wherein the concentration of the metal-solvent catalyst is from 3 wt % to less than 6 wt %.

4. The polycrystalline diamond anvil of claim 1, wherein the plurality of diamond grains and the metal-solvent catalyst collectively exhibit a coercivity from 155 Oe to 175 Oe.

5. The polycrystalline diamond anvil of claim 1, wherein the plurality of diamond grains and the metal-solvent catalyst collectively exhibit a coercivity from 115 Oe to 175 Oe.

6. The polycrystalline diamond anvil of claim 1, wherein the plurality of diamond grains and the metal-solvent catalyst collectively exhibit a coercivity from 155 Oe to 175 Oe.

7. The polycrystalline diamond anvil of claim 1, wherein the plurality of diamond grains and the metal-solvent catalyst collectively exhibit a specific magnetic saturation of from about 5 G·cm$^3$/g to about 15 G·cm$^3$/g.

8. The polycrystalline diamond anvil of claim 1, wherein the plurality of diamond grains and the metal-solvent catalyst collectively exhibit a specific magnetic saturation of from about 10 G·cm$^3$/g to about 15 G·cm$^3$/g.

9. The polycrystalline diamond anvil of claim 1, wherein a ratio of the specific magnetic saturation to the coercivity is about 0.060 to about 0.090.

10. The polycrystalline diamond anvil of claim 1, wherein the plurality of bonded diamond grains are bonded by a high-pressure/high-temperature process at a temperature from about 1200° C. to about 1450° and a pressure of at least about 7.5 GPa.

11. The polycrystalline diamond anvil of claim 1, wherein the plurality of bonded diamond grains and the metal-solvent catalyst collectively exhibit an x-ray transparency sufficient for performing x-ray analysis of a sample during compression by at least the polycrystalline diamond anvil.

12. An ultra-high pressure apparatus, comprising:
a plurality of polycrystalline diamond anvils arranged to compress a sample, at least one of the plurality of polycrystalline diamond anvils comprising:
a plurality of bonded diamond grains directly bonded together and defining a plurality of interstitial regions, the plurality of bonded diamond grains having an average grain size of 30 µm or less;
a metal-solvent catalyst occupying at least a portion of the plurality of interstitial regions, the metal-solvent catalyst present in a concentration from 1 weight % to 6 weight %;
wherein the plurality of diamond grains and the metal-solvent catalyst collectively exhibit a coercivity from 115 Oe to 250 Oe; and
wherein the plurality of diamond grains and the metal-solvent catalyst collectively exhibit a specific magnetic saturation of about 15 G·cm$^3$/g or less.

13. The ultra-high pressure apparatus of claim 12, wherein the concentration of the metal-solvent catalyst is 1 wt % to 3 wt %.

14. The ultra-high pressure apparatus of claim 12, wherein the concentration of the metal-solvent catalyst is from 3 wt % to less than 6 wt %.

15. The ultra-high pressure apparatus of claim 12, wherein the plurality of diamond grains and the metal-solvent catalyst collectively exhibit a coercivity from 155 Oe to 175 Oe.

16. The ultra-high pressure apparatus of claim 12, wherein the plurality of diamond grains and the metal-solvent catalyst collectively exhibit a coercivity from 115 Oe to 175 Oe.

17. The ultra-high pressure apparatus of claim 12, further comprising at least one piston operable to drive one or more of the plurality of polycrystalline diamond anvils to compress the sample between the plurality of polycrystalline diamond anvils.

18. The ultra-high pressure apparatus of claim 12, wherein the plurality of polycrystalline diamond anvils are configured as first stage anvils, and further comprising a plurality of second stage polycrystalline diamond anvils.

19. The ultra-high pressure apparatus of claim 12, wherein the plurality of bonded diamond grains and the metal-solvent catalyst collectively exhibit an x-ray transparency sufficient for performing x-ray analysis of a sample during compression by the plurality of polycrystalline diamond anvils.

* * * * *